(12) United States Patent
Jalink et al.

(10) Patent No.: US 7,435,876 B2
(45) Date of Patent: Oct. 14, 2008

(54) METHOD AND A DEVICE FOR MAKING IMAGES OF THE QUANTUM EFFICIENCY OF THE PHOTOSYNTHETIC SYSTEM WITH THE PURPOSE OF DETERMINING THE QUALITY OF PLANT MATERIAL AND A METHOD AND A DEVICE FOR MEASURING, CLASSIFYING AND SORTING PLANT MATERIAL

(75) Inventors: Hendrik Jalink, Wageningen (NL); Rob Van Der Schoor, Wageningen (NL); Adrianus Henricus Cornelis Maria Schapendonk, Wageningen (NL)

(73) Assignee: Plant Research International B.V., Wageningen (NL)

( * ) Notice: Subject to any disclaimer, the term of this patent is extended or adjusted under 35 U.S.C. 154(b) by 85 days.

(21) Appl. No.: 10/533,447

(22) PCT Filed: Oct. 31, 2003

(86) PCT No.: PCT/NL03/00750

§ 371 (c)(1),
(2), (4) Date: Nov. 28, 2005

(87) PCT Pub. No.: WO2004/040274

PCT Pub. Date: May 13, 2004

(65) Prior Publication Data

US 2006/0102851 A1 May 18, 2006

(30) Foreign Application Priority Data

Oct. 31, 2002 (NL) ................................. 1021800

(51) Int. Cl.
*A01H 9/00* (2006.01)

(52) U.S. Cl. ..................................... 800/295

(58) Field of Classification Search ............... None
See application file for complete search history.

(56) References Cited

FOREIGN PATENT DOCUMENTS

| EP | 0 333 561 A | | 9/1989 |
|---|---|---|---|
| EP | 1 125 111 A | | 8/2001 |
| WO | WO 01/000333 | * | 1/2001 |
| WO | WO 01/000333 A | | 1/2001 |

OTHER PUBLICATIONS

Hak et al. Radiat Environ Biophys 1990 29:329-336.*
Szabo et al. Radiat Environ Biophys 1992 31:153-160.*
B. Genty, S. Meyer: "Quantitative mapping of leaf photosynthesis using chlorophyll flourescence imaging", Australian Journal of Plant Physiology, 1994, pp. 277-284, XP008018804 cited in the application, p. 278, left-hand column, paragraph 2, p. 278, left-hand column, last line—right-hand column, paragraph 4.
Schreiber U: "Detection of rapid introductio kinetics with a new type of high frequency modulated chlorophyll flourometer", Photosynthesis Research, Dordrecht, NL, vol. 9, No. 9, 1986, pp. 261-272, XP002119608, ISSN: 0166-8595 cited in the application the whole document.

* cited by examiner

*Primary Examiner*—Jon P Weber
*Assistant Examiner*—Bin Shen
(74) *Attorney, Agent, or Firm*—Young & Thompson

(57) ABSTRACT

A method for determining the quality of plant material by making chlorophyll fluorescence images of the material by scanning the material with a beam of electromagnetic radiation so that the chlorophyll present is excited, and measuring the chlorophyll fluorescence with an imaging detector. From the fluorescence images obtained with a fast and a slow scan, the image of the quantum efficiency of the photosynthetic system of the plant material is calculated. A device for measuring the chlorophyll fluorescence images and a method and devices for sorting and classifying plant material are also described.

9 Claims, 1 Drawing Sheet

Figure 1:
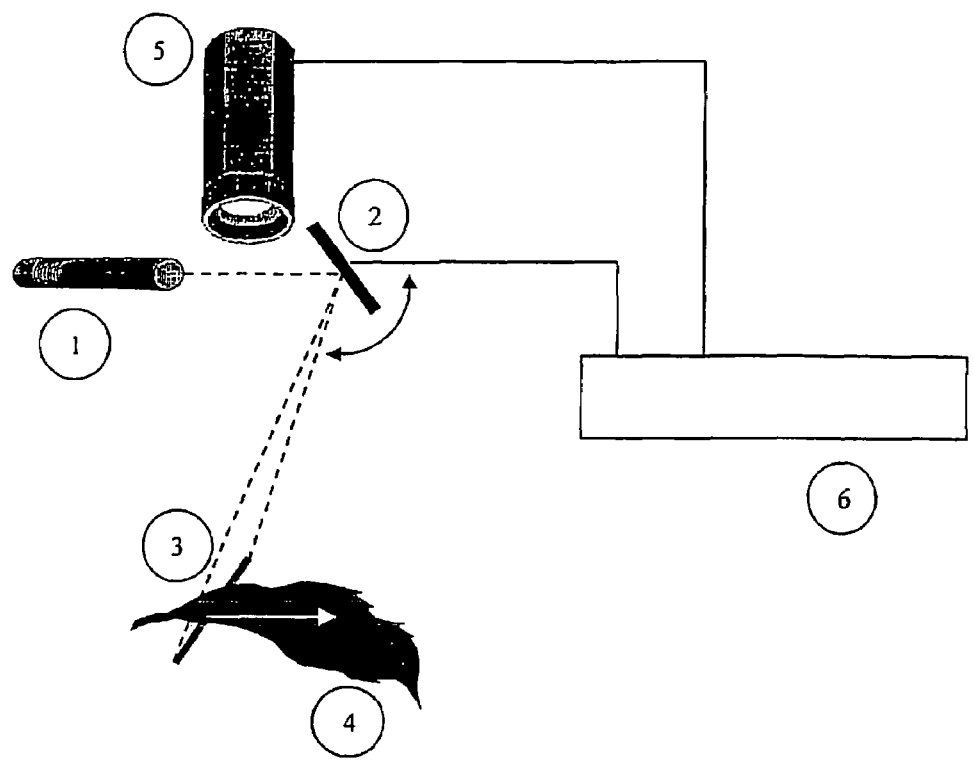

METHOD AND A DEVICE FOR MAKING IMAGES OF THE QUANTUM EFFICIENCY OF THE PHOTOSYNTHETIC SYSTEM WITH THE PURPOSE OF DETERMINING THE QUALITY OF PLANT MATERIAL AND A METHOD AND A DEVICE FOR MEASURING, CLASSIFYING AND SORTING PLANT MATERIAL

BACKGROUND OF THE INVENTION

1. Field of the Invention

This application is a 371 of PCT/NL03/00750 filed Oct. 31, 2003.

The present invention relates to a method for determining the quality of plant material, such as for instance whole plants, leaf material, fruits, berries, flowers, flower organs, roots, seeds, bulbs, algae, mosses and tubers of plants, by making chlorophyll fluorescence images, particularly a method wherein a characteristic chlorophyll fluorescence image is calculated from the measured chlorophyll fluorescence images and more particularly a method wherein said characteristic fluorescence image contains information about the quantum efficiency of the photosynthetic activity of photosynthetic system of the plant material. The present invention further relates to a device for measuring the chlorophyll fluorescence images and calculating the image of the quantum efficiency of the photosynthetic activity of the photosynthetic system of the plant material from said chlorophyll fluorescence images. The present invention also relates to a device for sorting and classifying plant material on the basis of the chlorophyll fluorescence images and the image of the quantum efficiency of the photosynthetic activity of the photosynthetic system of the plant material calculated from said chlorophyll fluorescence images.

2. Description of the Related Art

The common method of measuring the quantum efficiency of the photosynthetic activity of plant material, is measuring the photosynthetic activity using U. Schreiber's pulse amplitude modulation (PAM) fluorometer described in "Detection of rapid induction kinetics with a new type of high frequency modulated chlorophyll fluorometer" Photosynthesis Research (1986) 9: 261-272. In this method the quantum efficiency of the photosynthetic activity is determined. To that end first the fluorescence yield, FO, is measured in the dark or at a low light intensity of the ambient light. Then the maximum fluorescence yield, Fm, is determined at a saturating light pulse. From the two measuring signals the efficiency of the photosynthetic system can be calculated according to $Q=(Fm-FO)/Fm$. Said measuring method determines the efficiency of the photosynthetic system of a small surface of a leaf, a so-called spot measurement and therefore is not imaging.

Known measuring methods that are imaging, work according to the same principle as the PAM fluorometer. A known measuring method is the one of B. Genty and S. Meyer, described in "Quantitative mapping of leaf photosynthesis using chlorophyll fluorescence imaging" Australian Journal of Plant Physiology (1995) 22: 277-284. In this method the surface of the plant material, for instance a leaf, is irradiated in short pulses with electromagnetic radiation from a lamp and the fluorescence is measured during the pulses with a camera system. Said first measurement takes place in the dark or at a low light intensity and results in the FO measurement. The next measurement is carried out at a saturating light pulse and results in the Fm measurement. From said measurements an image can be calculated of the efficiency of the photosynthetic system. A drawback of this method is that a large surface of for instance 50×50 $cm^2$ cannot be irradiated with a saturating light pulse. The present light sources are not bright enough to irradiate such a surface with sufficient light intensity.

SUMMARY OF THE INVENTION

It is an object of the present invention to provide a method for measuring the chlorophyll fluorescence in an imaging manner, and to determine the quantum efficiency of the photosynthetic activity of plant material from the obtained chlorophyll fluorescence images, wherein the drawback of the small measuring surface of the known measuring methods is overcome.

The present invention therefore provides a method for determining the quality of plant material by determining a chlorophyll fluorescence image of said plant material, wherein the plant material is irradiated with a beam of electromagnetic radiation comprising one or more such wavelengths that at least a part of the chlorophyll present is excitated by at least a part of the radiation, the beam of electromagnetic radiation having such a shape that only a small part of the plant material is irradiated, and the beam being moved over the plant material such that a larger part of the plant material is measured, wherein the fluorescence radiation originating from the plant material associated with the chlorophyll transition, is measured with an imaging detector for obtaining a chlorophyll fluorescence image.

Preferred is such a method, wherein, in any given order, during a certain duration of time several fast scans are made over the plant material with the electromagnetic beam for obtaining a chlorophyll fluorescence image Ffast, and during a certain duration of time a slow scan is made over the plant material with the electromagnetic beam for obtaining a chlorophyll fluorescence image Fslow, and subsequently the characteristic chlorophyll fluorescence image that is a measure for the efficiency of the photosynthetic system of plant material is calculated from the chlorophyll fluorescence images Ffast and Fslow.

Preferably the characteristic chlorophyll fluorescence image contains information about the quantum efficiency of the photosynthetic activity of the photosynthetic system of the plant material and this image is calculated with the formula $IQP=(Fslow-Ffast)/Fslow$.

BRIEF DESCRIPTION OF THE DRAWING FIGURES

FIG. 1 schematically shows a device for making chlorophyll fluorescence images and determining the quantum efficiency of the photosynthetic activity of plant material.

Figure 2:
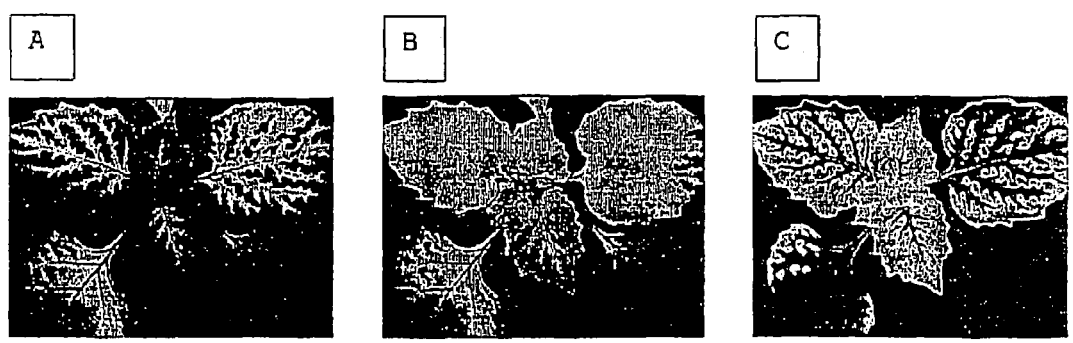

FIG. 2 shows three chlorophyll fluorescence images that have been obtained using a device according to FIG. 1 for black nightshade. Panel A shows the result of a number of fast scans; panel B shows the results of a slow scan; panel C shows the result of the quantum efficiency of the photosynthetic activity, calculated from the images of panel A and B.

DETAILED DESCRIPTION

The present invention is based on a spectroscopic measurement which is highly specific to the chlorophyll present and the functioning of the photosynthetic system. The functioning of the photosynthetic system is very important to the proper functioning of a plant and the quality of the plant. Light is captured by the chlorophyll molecules. If the plant is of a good quality and is not subjected to stress, the captured energy of the chlorophyll molecules will quickly be passed on to the photosynthetic system for conversion into chemical energy. Chlorophyll has the property that it shows fluorescence. When the energy can be processed sufficiently fast by the photosynthetic system this results in a low level of fluorescence light. When the photosynthetic system cannot process the energy sufficiently fast, the fluorescence light will increase in intensity. When upon switching on a saturating light source having electromagnetic radiation which is absorbed by the chlorophyll, the photosynthetic system is able to process the energy fast, the duration of time from switching on the light source until the maximum level of the irradiated fluorescence will be much longer, than would be the case when the photosynthetic system is not able to process the energy fast. This property is now utilised to determine the quantum efficiency of the photosynthetic activity. The method of the invention makes it possible to measure the quantum efficiency of the photosynthetic activity of whole plants in an imaging manner.

In the method of the invention plant material is irradiated with electromagnetic radiation having such a wavelength that at least a part of the chlorophyll present is excited, for instance with electromagnetic radiation having a wavelength of between 200 and 750 nm, such as laser light having a wavelength of approximately 670 nm. The fluorescence is measured with an imaging detector, for instance with a camera, between 600 and 800 nm, for instance around 730 nm. The beam of electromagnetic radiation may for instance be obtained by using a laser producing a diverging laser beam which is scanned over the plant material by means of a moving mirror, for instance a rotatable mirror mounted on a galvanometer and controlled by a computer. The plant material can now first be scanned fast with the laser line with a frequency of between approximately 1 Hz and approximately 10 kHz, for instance with a frequency of 50 Hz, during for instance 10 seconds. During those 10 seconds the fluorescence is measured by an imaging detector. This image is called the Ffast measurement which is transmitted to the computer. Subsequently a slow scan can be made with a frequency of between approximately 0.01 and approximately 1 Hz, for instance a frequency of 0.1 Hz during a same duration of time of 10 seconds. During said 10 seconds the fluorescence is measured again by an imaging detector. Said image is called the Fslow measurement and it is also transmitted to the computer. From these two images the quantum efficiency of the photosynthetic activity (Imaging Quantum efficiency of Photosynthesis: IQP) can be calculated according to:

$$IQP = (Fslow - Ffast)/Fslow \quad (1)$$

The computer carries out the calculation according to formula (1) for each image pixel of the plant material. This results in the characteristic chlorophyll fluorescence image as an intensity distribution of the quantum efficiency of the photosynthetic system of the plant material. If during the measurement the duration of time of the fast scan is riot the same as the duration of time of the slow scan the calculation has to be corrected therefore.

For irradiating the plant material a laser, lamp or LED lamp can be used which irradiates the plant material with electromagnetic radiation in the shape of a thin line or another shape, such that during a scan with the electromagnetic radiation over the plant material a small part of the plant material is irradiated and in a scan by moving the mirror a larger part of the plant material or the entire plant material is irradiated during a certain duration of time. Any movable or rotatable mirror can be used as the mirror, such that the electromagnetic radiation is reflected by the mirror and scanned over the plant material. An electrically controlled galvanometer, a movable mirror on spring steel, a polygon mirror or another known structure can be used for moving the mirror. The fluorescence radiation originating from the plant material can be measured with any suitable imaging detector, for instance a video camera, CCD-camera, line scan camera or a number of photodiodes or photomultipliers.

The intensity and width and length of the electromagnetic radiation, or the power of the electromagnetic radiation per surface unit, which is scanned over the plant material, are preferably selected such that the photosynthetic system during a slow scan is saturated. The frequencies associated with a slow and fast scan are selected such that the value calculated for the quantum efficiency of the photosynthetic activity according to formula (1) corresponds within certain limits with a measurement of Schreiber's PAM-fluorometer. The time it takes to make a slow scan can be taken as the duration of time of measuring a fast and slow scan.

The invention is highly sensitive, entirely non-destructive and imaging. These are the characteristics of the invention that enable one to make a sorting device or classifying device by which means plant material can be selected or classified on the basis of the IQP measurement. Because the IQP measurement has a direct relation to the quality of the plant material, sorting or classification on quality is possible.

The invention therefore also relates to a method for separating or classifying plant material consisting of individual components into several fractions each having a different quality, wherein a characteristic image parameter is determined for each component using a method or device for determining the quality of plant material according to the invention and the fractions of components having a characteristic image parameter in the same pre-determined range are collected.

The invention further relates to a device for separating plant material using the above-mentioned method, comprising a supply part for the plant material, a part for the irradiation, a part for the measuring of the fluorescence radiation originating from the plant material for obtaining the fluorescence image and image of the quantum efficiency of the photosynthetic activity and a separation part that works on the basis of the image measured.

The invention further relates to a method for classifying plant material using the above-mentioned method, comprising a moving structure for localising the plant material, for instance a moving carriage or robot arm, a part for the irradiation, a part for the measuring of the fluorescence radiation originating from the plant material for obtaining a fluorescence image of the quantum efficiency of the photosynthetic activity and a classification part that works on the basis of the image measured.

The material to be sorted or classified may consist of entire plants, cut flowers, leaf material, fruits, berries, vegetables, flowers, flower organs, roots, tissue culture, seeds, bulbs, algae, mosses and tubers of plants etc. The fractions into which the plant material is separated or classified, may each consist of individual entire plants, cut flowers, leaf material, fruits, berries, vegetables, flowers, flower organs, roots, tissue culture, seeds, bulbs, algae, mosses and tubers of plants etc.

The present invention can be used for refined purposes, such as early selection of seedlings on stress tolerance, programmed administering of herbicides and quality control in greenhouse culture. The method according to the invention can be used in the screening of the plant quality in the seedling stage at the grower's. Trays of seedlings can be tested. Seedlings of a low quality can be removed and replaced by good seedlings. The method according to the invention can also be used for selection of seedlings on stress sensitivity by subjecting the trays to infectious pressure or to abiotic stress factors and registering the signal build-up on-line. In this connection the specific demands that are made on the quality of seedlings by biological farming, are interesting. Damage to plant material due to diseases can be detected at a very early stage in the chlorophyll fluorescence image as a local increase of the fluorescence. This is detected in the IQP image as a local decrease of the quantum efficiency of the photosynthetic activity. At an auction plants can be checked on quality. A fast, non-destructive and objective method for determining the pot plant quality and the vase quality of the flowers supplied at the auction or even during cultivation is of great economic importance. The flower quality depends on the age, cultivation and possible post-harvest treatment that influence the IQP image. The method according to the invention can also be used in high-throughput-screening of model crops (Arabidopsis and rice) for functional genomics research for the purpose of function analysis and trait identification. Another important use of the new invention can be found in the determination of freshness of vegetables and fruits and the presence of damages, for instance in the form of diseases. Damages show a lower IQP value in the IQP image than the healthy parts of the plant material.

In general it has to be established from tests at what IQP value in the image sorting or classifying can take place. In a test of several stages of damages, the IQP value in the image of the damage is measured and divided into several classes. Subsequently during the growth or storage it is established which classes result in a high quality. The threshold value found in this test is used as the value of IQP to select on.

A preferred embodiment of a device for measuring the chlorophyll fluorescence images and calculating the image of the quantum efficiency of the photosynthetic activity is shown in FIG. 1. This is a simple form that the device may have. A laser having a wavelength of between 200 and 750 nm, and preferably of 670 nm, (1) produces a diverging laser beam which is reflected by a mirror (2) in the direction of the plant material (4). The mirror is mounted on a galvanometer and namely such that the mirror can rotate. The galvanometer is controlled by a computer (6) such that the laser line (3) which is generated by the laser can be scanned over the plant material. The laser line preferably has a length larger than the maximum width of the plant material. The laser line serves to excitate chlorophyll molecules. At least a part of the chlorophyll molecules gets into an electronically excited state. At least a part of the chlorophyll molecules falls back to the ground state under emitting fluorescence. The fluorescence is measured with a camera provided with an optical filter, suitable to transmit only light between 600 and 800 nm, for instance about 730 nm. The method now consists of first scanning a laser line over the object fast, for instance with a frequency of 50 Hz and during 10 seconds. During said 10 seconds the fluorescence is measured by the camera and read by the computer after the measurement. This image is called the Ffast measurement. Subsequently a slow scan is made using for instance a frequency of 0.1 Hz during the same duration of time of 10 seconds. During said 10 seconds the fluorescence is measured by the camera and read by the computer after the measurement. This image is called the Fslow measurement. From said two images the quantum efficiency of the photosynthetic system (IQP) is calculated according to formula (1) for each pixel of the image.

A skilled person will recognise that for obtaining the image of the quantum efficiency of the photosynthetic system the slow scan can also be carried out first.

A device for sorting plant material according to the invention may consist of a conveyor belt for the supply of plant material to the measuring part where the above-mentioned fluorescence measurement according to the invention is carried out after which the plant material is transported further to the separation part in which the fractions of which the IQP image is not within the predetermined limits, are removed from the conveyor belt in a manner that is known per se, for instance by means of an air flow. The air flow may be regulated by a valve controlled by an electronic circuit such as a microprocessor processing the signal of the measuring part. The plant material may also be separated in various classes of quality in which for each class of quality the IQP image of the plant material is within predetermined limits. The limits may be established by for instance determining the IQP image of samples of plant material having the wanted quality or properties. The person skilled in this field will know that the plant material to be separated can also be transported through the measuring part and the separation part in another way than by means of a conveyor belt and that various methods are available to sort the various fractions from the main flow, such as an air flow, liquid flow or mechanic valve. The plant material may for instance also be present in a liquid. Sorting in a liquid may for instance take place in order to minimise the risk of damaging very delicate plant material, such as apples, berries and other soft fruit.

It is further noted that a device for sorting or classifying plant material in for instance a greenhouse or in the field, according to the invention may consist of a device that runs past the plants and measures their IQP image and subsequently classifies them on quality and stores this in a data base or removes the plant material of inferior quality. The object of a data base is to get an insight into the quality of the entire lot and to enable to quickly retrieve the position of the plants that fall within a certain class of quality.

The above-mentioned preferred embodiment for the measurement can also be moved over the plant material by a robot arm or a known device such as a carriage, for the purpose of measuring deviations in the plant material, such as for instance early detection of diseases. Detection of diseases in for instance plants can be established because in a test it has been shown that due to the damage the fluorescence signal at the damaged spot is locally higher or the IQP value is lower than in the surrounding plant material. In tests it has also been established what quantity of fungicide has to be applied on the damaged spot to combat the disease. The present invention now allows detecting and locally controlling a disease by locally and in a highly dosed manner spraying the damage with a fungicide in an automated manner by using a nozzle. An advantage of the method used is the decrease of the quantity of fungicide, so that plants need not be sprayed with fungicide by way of prevention.

It is also noted that the device can be used for controlling the cultivation of plants by coupling the greenhouse climate control to the information obtained with the method as described above. An advantage of the present invention is that the entire plant is imaged and thus a good measure for the quantum efficiency of the photosynthetic activity can be calculated, this as opposed to the PAM fluorometer which only measures a small part of a leaf.

The invention can be used in any sorting device for plants or fruit. It is possible to build it in into every sorting device and carriages or robots that may or may not be automatically propelled.

EXAMPLE 1

This example describes the effect of a herbicide treatment on the chlorophyll fluorescence image and the image of the quantum efficiency of the photosynthetic activity. The fluorescence images were measured using the above-mentioned preferred embodiment according to FIG. 1.

FIG. 2A shows the result of the chlorophyll fluorescence image of the fast scan of a black nightshade plant on which 48 hours previously, on each of a number of leaves a drop of 3 μl of herbicide solution was applied. The herbicide activity is visible in the image in the local lighter shade of the leaves. FIG. 2B shows the result of the slow scan of the same plant. The image of the quantum efficiency of the photosynthetic activity is calculated with a computer for each pixel of the image according to formula (1) from the images 2A and 2B. The dark areas in the image of the leaves are hardly photosynthetically active. The pixels have a value of between 0 and 0.3. The healthy parts of the plant indeed show a normal value of the quantum efficiency of the photosynthetic activity. The pixels have a value of between 0.7 and 0.85. They can be recognised by the light areas. From tests it is known at what threshold values for the quantum efficiency of the photosynthetic activity the leaves die. Above a certain threshold value of the quantum efficiency of the photosynthetic activity those plant parts are still healthy. Below a certain threshold value those plant parts die. From this test it appeared that the threshold value was approximately 0.5. An advantage of the present invention is that now the entire plant is measured and therefore a proper judgement can be made of the total quantum efficiency of the photosynthetic activity of the entire plant. This as opposed to the methods known up until now in which at a number of spots of the plant a spot measurement is carried out or only a small part of the plant is imaged.

The invention claimed is:

1. A method for determining the quantum efficiency of the photosynthetic system of a plant, comprising:
   determining a chlorophyll fluorescence image of said plant material, by irradiating the plant material with a beam of electromagnetic radiation comprising one or more wavelengths such that at least a part of the chlorophyll present is excitated by at least a part of the radiation, the beam of electromagnetic radiation having such a shape that only a part of the plant material is initially arradiated, and the beam being moved over the plant material such that further parts of the plant material are irradiated, wherein fluorescence radiation originating from the plant material associated with chlorophyll transition, is measured with an imaging detector for obtaining a chlorophyll fluorescence image, wherein:
   during a certain duration of time, several fast scans are made over the plant material with the electromagnetic beam for obtaining a chlorophyll fluorescence image Ffast, and
   during a certain duration of time, a slow scan is made over the plant material with the electromagnetic beam for obtaining a chlorophyll fluorescence image Fslow, and subsequently
   obtaining a characteristic chlorophyll fluorescence image that is a measure for the quantum efficiency of the photosynthetic system of plant material and is calculated from the chlorophyll fluorescence images Ffast and Fslow.

2. The method according to claim 1, wherein the characteristic chlorophyll fluorescence image containing information about the quantum efficiency of the photosynthetic activity of the photosynthetic system of the plant material is calculated with the formula:

$$IQP = (F\text{slow} - F\text{fast})/F\text{slow}.$$

3. The method according to claim 1, the beam having the shape of a thin line.

4. The method according to claim 1, the beam being moved over the plant material such that the entire surface of the plant material is irradiated.

5. The method according to claim 1, the electromagnetic radiation used for irradiating the plant material having a wavelength of between 200 and 750 nm.

6. The method according to claim 1, the electromagnetic radiation used for irradiating the plant material being generated by a lamp, laser or LED-lamp.

7. The method according to claim 1, the fluorescence radiation originating from the plant material being measured between 600 and 800 nm.

8. The method according to claim 1, the fluorescence radiation originating from the plant material being measured with an electronic camera consisting of a video camera, CCD-camera, line scan camera or a number of photodiodes or photomultipliers.

9. The method according to claim 1, wherein:
   the characteristic chlorophyll fluorescence image containing information about the quantum efficiency of the photosynthetic activity of the photosynthetic system of the plant material and this image is calculated with the formula:

$$IQP = (F\text{slow} - F\text{fast})/F\text{slow};$$

the beam having the shape of a thin line and being moved over the plant material such that the entire surface of the plant material is irradiated,
   said electromagnetic radiation being generated by a lamp, laser or LED-lamp and having a wavelength of between 200 and 750 nm, and
   said fluorescence being measured between 600 and 800 nm with an electronic camera consisting of a video camera, CCD-camera, line scan camera or a number of photodiodes or photomultipliers.

* * * * *